(12) United States Patent
McKinley et al.

(10) Patent No.: US 8,439,830 B2
(45) Date of Patent: May 14, 2013

(54) CANNULA WITH INTEGRATED CAMERA AND ILLUMINATION

(75) Inventors: Arthur C. McKinley, Westport, MA (US); Melvin B. Prenovitz, Brookline, MA (US); Philip E. McKinley, Westford, MA (US); Jesse R. Plouffe, Wilmington, MA (US)

(73) Assignee: EndoSphere Surgical, Inc., Brookline, MA (US)

( * ) Notice: Subject to any disclaimer, the term of this patent is extended or adjusted under 35 U.S.C. 154(b) by 274 days.

(21) Appl. No.: 12/748,062

(22) Filed: Mar. 26, 2010

(65) Prior Publication Data
US 2010/0249512 A1    Sep. 30, 2010

Related U.S. Application Data

(60) Provisional application No. 61/164,215, filed on Mar. 27, 2009, provisional application No. 61/261,910, filed on Nov. 17, 2009.

(51) Int. Cl.
*A61B 1/05* (2006.01)
(52) U.S. Cl.
USPC .............. 600/173; 600/129; 600/179
(58) Field of Classification Search .......... 600/109, 600/111, 129, 128, 166, 173, 175, 179; 348/45, 348/65
See application file for complete search history.

(56) References Cited

U.S. PATENT DOCUMENTS

| | | | |
|---|---|---|---|
| 4,858,001 A | 8/1989 | Milbank et al. | |
| 5,166,787 A * | 11/1992 | Irion | 348/75 |
| 5,167,221 A * | 12/1992 | Chikama | 600/149 |
| 5,183,471 A | 2/1993 | Wilk | |
| 5,256,149 A | 10/1993 | Banik et al. | |
| 5,305,121 A | 4/1994 | Moll | |
| 5,381,784 A * | 1/1995 | Adair | 600/166 |
| 5,443,484 A | 8/1995 | Kirsch et al. | |
| 5,448,990 A | 9/1995 | De Faria-Correa | |
| 5,538,497 A * | 7/1996 | Hori | 600/182 |
| 5,569,160 A | 10/1996 | Sauer et al. | |
| 5,588,949 A | 12/1996 | Taylor et al. | |
| 5,653,677 A * | 8/1997 | Okada et al. | 600/112 |
| 5,720,761 A * | 2/1998 | Kaali | 606/185 |

(Continued)

FOREIGN PATENT DOCUMENTS

EP    0556056 A1    8/1993

OTHER PUBLICATIONS

Cadeddu, J. et al., "Novel magnetically guided intra-abdominal camera to facilitate laparoendoscopic single-site surgery: initial human experience," Surg. Endoc. (2009) 23: 1894-1899.

(Continued)

*Primary Examiner* — John P Leubecker
(74) *Attorney, Agent, or Firm* — Goodwin Procter LLP

(57) ABSTRACT

A cannula assembly includes a tubular element forming a lumen, a deployable portion of the tubular element, and an electronic component mounted to the deployable portion of the tubular element. The tubular element has a proximal end and a distal end adapted to be inserted into a body cavity. The deployable portion of the tubular element is engaged near the distal end of the tubular element so as to transition between a closed position and an open position. The electronic component is at least partially disposed in the lumen when the deployable portion is in the closed position.

23 Claims, 10 Drawing Sheets

U.S. PATENT DOCUMENTS

| | | | | |
|---|---|---|---|---|
| 5,791,231 | A | 8/1998 | Cohn et al. | |
| 5,797,943 | A | 8/1998 | Danks et al. | |
| 5,860,996 | A | 1/1999 | Urban et al. | |
| 5,891,013 | A | 4/1999 | Thompson | |
| 5,899,851 | A * | 5/1999 | Koninckx | 600/117 |
| 5,957,832 | A | 9/1999 | Taylor et al. | |
| 6,097,423 | A | 8/2000 | Mattsson-Boze et al. | |
| 6,348,034 | B1 | 2/2002 | Thompson | |
| 6,371,909 | B1 | 4/2002 | Hoeg et al. | |
| 6,387,043 | B1 * | 5/2002 | Yoon | 600/109 |
| 6,478,730 | B1 | 11/2002 | Bala et al. | |
| 6,508,759 | B1 | 1/2003 | Taylor et al. | |
| 6,527,704 | B1 | 3/2003 | Chang et al. | |
| 6,648,816 | B2 * | 11/2003 | Irion et al. | 600/173 |
| 6,767,321 | B2 | 7/2004 | Czarnek et al. | |
| 6,863,651 | B2 | 3/2005 | Remijan et al. | |
| 6,916,286 | B2 * | 7/2005 | Kazakevich | 600/173 |
| 6,984,203 | B2 | 1/2006 | Tartaglia et al. | |
| 6,986,738 | B2 * | 1/2006 | Glukhovsky et al. | 600/109 |
| 7,037,258 | B2 * | 5/2006 | Chatenever et al. | 600/109 |
| 7,041,052 | B2 | 5/2006 | Saadat et al. | |
| 7,066,879 | B2 | 6/2006 | Fowler et al. | |
| 7,322,934 | B2 * | 1/2008 | Miyake et al. | 600/173 |
| 7,585,273 | B2 * | 9/2009 | Adler et al. | 600/117 |
| 7,604,648 | B2 | 10/2009 | Kerr | |
| 7,927,272 | B2 * | 4/2011 | Bayer et al. | 600/129 |
| 8,083,667 | B2 * | 12/2011 | Cooper et al. | 600/104 |
| 8,105,233 | B2 * | 1/2012 | Abou El Kheir | 600/166 |
| 2002/0049367 | A1 * | 4/2002 | Irion et al. | 600/173 |
| 2003/0055319 | A1 | 3/2003 | Chang | |
| 2003/0236505 | A1 | 12/2003 | Bonadio et al. | |
| 2005/0029978 | A1 | 2/2005 | Oleynikov et al. | |
| 2005/0059862 | A1 | 3/2005 | Phan | |
| 2005/0085691 | A1 * | 4/2005 | Nakao | 600/128 |
| 2005/0154256 | A1 | 7/2005 | Breidenthal et al. | |
| 2005/0182293 | A1 | 8/2005 | Katzman | |
| 2005/0234296 | A1 * | 10/2005 | Saadat et al. | 600/129 |
| 2006/0069314 | A1 * | 3/2006 | Farr | 600/179 |
| 2006/0106286 | A1 * | 5/2006 | Wendlandt et al. | 600/173 |
| 2006/0183095 | A1 | 8/2006 | Korndorffer et al. | |
| 2006/0252994 | A1 * | 11/2006 | Ratnakar | 600/173 |
| 2007/0032701 | A1 | 2/2007 | Fowler et al. | |
| 2007/0073109 | A1 * | 3/2007 | Irion | 600/179 |
| 2007/0093812 | A1 * | 4/2007 | Hayashida et al. | 606/46 |
| 2007/0179430 | A1 | 8/2007 | Smith et al. | |
| 2007/0249899 | A1 | 10/2007 | Seifert | |
| 2008/0027279 | A1 * | 1/2008 | Abou El Kheir | 600/111 |
| 2008/0065099 | A1 | 3/2008 | Cooper et al. | |
| 2008/0147018 | A1 | 6/2008 | Squilla et al. | |
| 2008/0208006 | A1 * | 8/2008 | Farr | 600/178 |
| 2008/0269557 | A1 | 10/2008 | Marescaux et al. | |
| 2008/0269562 | A1 | 10/2008 | Marescaux et al. | |
| 2009/0012530 | A1 | 1/2009 | Fowler | |
| 2009/0018400 | A1 | 1/2009 | Raymond et al. | |
| 2009/0036744 | A1 | 2/2009 | Vayser | |
| 2009/0259097 | A1 | 10/2009 | Thompson | |
| 2009/0259102 | A1 | 10/2009 | Koninckx et al. | |
| 2009/0275799 | A1 | 11/2009 | Saadat et al. | |
| 2009/0312773 | A1 | 12/2009 | Cabrera et al. | |
| 2010/0010504 | A1 | 1/2010 | Simaan et al. | |
| 2010/0081875 | A1 * | 4/2010 | Fowler et al. | 600/114 |
| 2010/0185197 | A1 * | 7/2010 | Sakao et al. | 606/51 |
| 2010/0280316 | A1 * | 11/2010 | Dietz et al. | 600/109 |

OTHER PUBLICATIONS

Fowler, D.L. et al., "Initial trial of a stereoscopic, insertable, remotely controlled camera for minimal access surgery," Surg. Endosc. (2010) 24:9-15.

International Search Report and Written Opinion for International Application No. PCT/US2010/028881 mailed on Oct. 29, 2010.

http://www.karlstorz-hd-endoscopy.com, 1 page. (accessed Jan. 27, 2011.).

* cited by examiner

CANNULA WITH INTEGRATED CAMERA AND ILLUMINATION

CROSS-REFERENCE TO RELATED APPLICATIONS

This application claims priority to co-pending U.S. provisional patent application Ser. No. 61/164,215, titled "Cannula with embedded camera and illumination," filed on Mar. 27, 2009, and U.S. provisional patent application Ser. No. 61/261,910, titled "Shape Memory Alloy Group, applications including SMA Clips, closures and Endoscope steering," filed on Nov. 17, 2009, the disclosures of both of which are herein incorporated by reference in their entireties.

TECHNICAL FIELD

The present invention relates generally to cannulas with integrated imaging and illumination devices, more particularly to those configured with a deployable portion.

BACKGROUND

In minimally invasive surgery, there are often several small incisions made into the body to insert surgical tools, insufflation devices, endoscopes, or other viewing devices. Surgeons are now doing procedures in a manner that minimizes the number of incisions, possibly to only one, referred to as Single Port Incision or Single Port Access (SPA). Surgeons are also using natural orifices, such as the mouth, to provide access for procedures using no incision or only incisions internal to the body.

The advantages sought by surgeons by reducing the number of incision points to as few as possible is to lessen trauma to the patient, reduce the incidence of infection, improve recovery time, and decrease cosmetic damage.

The reduction of incision locations will change the way that surgeons and their teams work. There may no longer be room around the access point to accommodate multiple surgeons who would normally hold and adjust instruments around the surgical field. A single surgeon may need to control all of the instruments for the procedure through one access point.

For example, endoscopic surgical procedures performed through a tubular cannula have evolved over the years. Presently, surgeons are performing endoscopic procedures in any hollow viscus of the torso body area after the region is insufflated. Typically, multiple narrow cannulas are each inserted through individual small entrance wounds (i.e., ports) in the skin, in order to accommodate various instruments, as well as varying viewing angles. To accomplish their insertion, separate trocars are used in conjunction with the cannulas to puncture the body cavity. A trocar is a guide placed inside the cannula with either a pointed cutting blade or blunt tip, depending on whether it is used to puncture the skin or enter through a separately made incision. Once the cannula is inserted, the trocar is removed, leaving the hollow cannula in place for use during the procedure.

The entry and deployment of imaging and/or lighting components can aid surgical procedures, such as endoscopic procedures. Examples of tubular cannula with deployable imaging and/or lighting components are described in U.S. Pat. No. 5,166,787 to Irion, U.S. Application Publication No. 2009/0275799 to Saadat et al., U.S. Application Publication No. 2009/0259097 to Thompson, and U.S. Application Publication. No. 2008/0065099 to Cooper et al., the disclosures of all of which are herein incorporated by reference in their entireties.

There is, therefore, a need in the art for a surgical apparatus assembly combining trocar cannula, with imaging and illumination capabilities, in order to minimize the number of openings in the body per procedure.

SUMMARY OF THE INVENTION

Prior art surgical instruments lack the ability to protect the optics of both imagers and illumination during insertion and lack the ability to obtain a viewing angle that is offset from the cannula axis. One purpose of the present invention is to make it easier to control the access, imaging, and instrument use during minimally invasive surgery, when using fewer incisions than typically necessary. By combining the cannula, imaging, and illumination, a single device can take the place of several, thereby allowing more efficient and more easily controlled access.

In one embodiment of the invention, a surgical apparatus includes combinations of trocar, cannula, and imaging and illumination components. In this embodiment, such combinations provide the surgeon with improved viewing of the surgical cavity. Alternative embodiments allow for reduced number of incisions on a patient.

The apparatus also allows for the development of improved surgical methods including reduced number of incisions, improved imaging of the surgical cavity, and/or improved performance of surgical effectiveness.

In one aspect, the invention relates to a cannula having a tubular element forming a lumen, such that the tubular element has a proximal end and a distal end adapted to be inserted into a body cavity. The cannula assembly includes a deployable portion of the tubular element, engaged near the distal end of the tubular element so as to transition between a closed position and an open position. The cannula assembly includes an electronic component mounted to the deployable portion of the tubular element, such that the electronic component is at least partially disposed in the lumen when the deployable portion is in the closed position.

In an embodiment of the foregoing aspect, the open position includes a range of positions. In another embodiment, the electronic component is disposed remotely from the lumen when the deployable portion is in the open position. In yet another embodiment, the deployable portion includes a wall portion of the tubular element. In still another embodiment, the cannula assembly also includes a removable trocar adapted to fit into the lumen when the deployable portion is in the closed position. In an embodiment, the deployable portion forms a pointed tip at the distal end of the tubular element when the deployable portion is in the closed position. In another embodiment, the pointed tip includes an optically transparent material, so as to project an image through the pointed tip onto the electronic component when the deployable portion is in the closed position.

In yet another embodiment of the above aspect, the electronic component can be an image transmission component, an illumination component, and combinations thereof. In still another embodiment, the image transmission component can be a charge-coupled device camera, a complementary metal oxide semiconductor imaging device, and a fiber optic cable. In an embodiment, the illumination component can be a light source and a fiber optic cable. In another embodiment, the light source can be a light emitting diode, an organic light emitting diode, a filament lamp, an electroluminescent source, and a laser source.

In still another embodiment of the above aspect, the deployable portion of the tubular element transitions between the open position and the closed position via a hinge arrangement. In an embodiment, the hinge arrangement is disposed in the tubular element. In another embodiment, the hinge arrangement includes a pivot. In yet another embodiment, the hinge arrangement is disposed on a circumference of the tubular element. In still another embodiment, the hinge arrangement includes a circumferential hinge. In an embodiment, the hinge arrangement is disposed on an exterior of the tubular element. In another embodiment, the hinge arrangement includes at least one four-bar linkage.

In yet another embodiment of the foregoing aspect, the cannula assembly also includes an actuation mechanism configured to transition the deployable portion between the closed position and the open position. In another embodiment, the actuation mechanism includes a knob disposed near the proximal end, at least one link coupled to the knob, and a hinge arrangement coupled to the at least one link and the deployable portion, such that rotation of the knob moves the deployable portion between the open position and the closed position.

In another aspect, the invention relates to a method of using a cannula assembly including inserting a tubular element with a lumen into a body cavity, such that the tubular element has a proximal end and a distal end, and actuating a deployable portion of the tubular element about the distal end from a closed position to an open position, such that an electronic component mounted to the deployable portion is at least partially disposed in the lumen when the deployable portion is in the closed portion and the lumen is substantially free from obstruction when the deployable portion is in the open position.

In an embodiment of the foregoing aspect, the method of using a cannula assembly also includes using the electronic component to view a portion of the body cavity beyond the distal end. In another embodiment, the method also includes passing at least one of a surgical tool and a second electronic component through the lumen beyond the distal end when the deployable portion is in the open position. In yet another embodiment, the method of using a cannula assembly also includes first introducing an insertion cannula into the body cavity such that the tubular element is inserted through the insertion cannula. In an embodiment, the method also includes withdrawing the cannula assembly from the body cavity through the insertion cannula such that a force exerted on the cannula assembly by the insertion cannula moves the deployable portion to the closed position.

BRIEF DESCRIPTION OF THE DRAWINGS

Other features and advantages of the present invention, as well as the invention itself, can be more fully understood from the following description of the various embodiments, when read together with the accompanying drawings, in which.

DETAILED DESCRIPTION

To provide an overall understanding of the invention, certain illustrative embodiments will now be described, including apparatus and methods for displaying images. However, it will be understood by one of ordinary skill in the art that the systems and methods described herein may be adapted and modified as is appropriate for the application being addressed and that the systems and methods described herein may be employed in other suitable applications. All such adaptations and modifications are to be considered within the scope of the invention.

Figure 1:
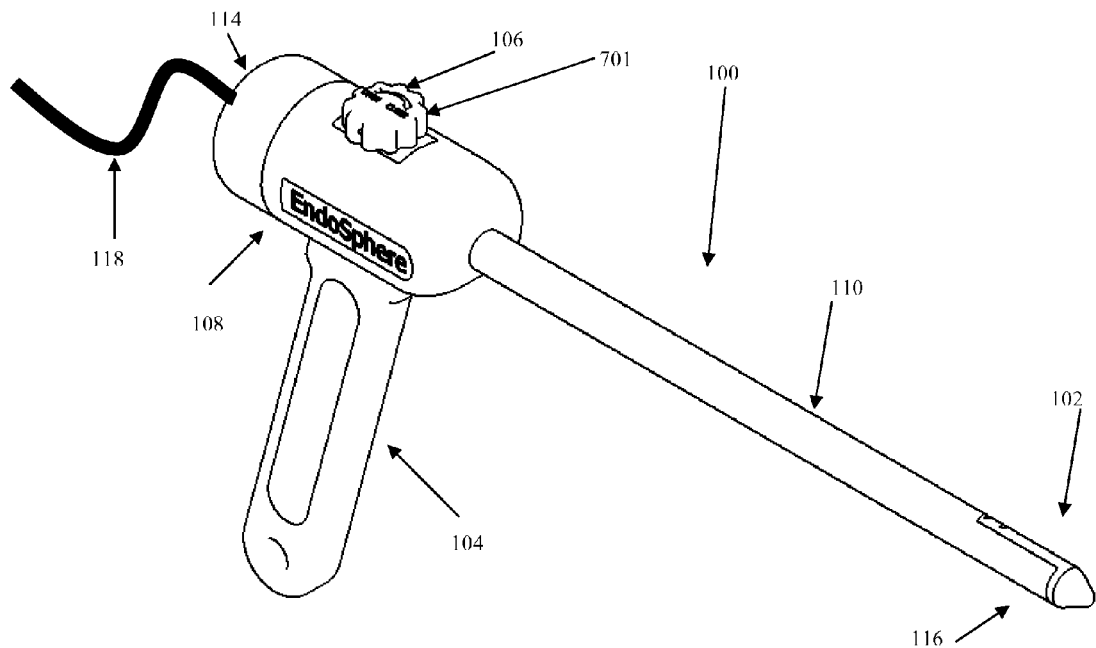
FIG. 1 depicts a schematic perspective view of a cannula assembly in a closed position, according to an embodiment of the present invention.
Figure 2:
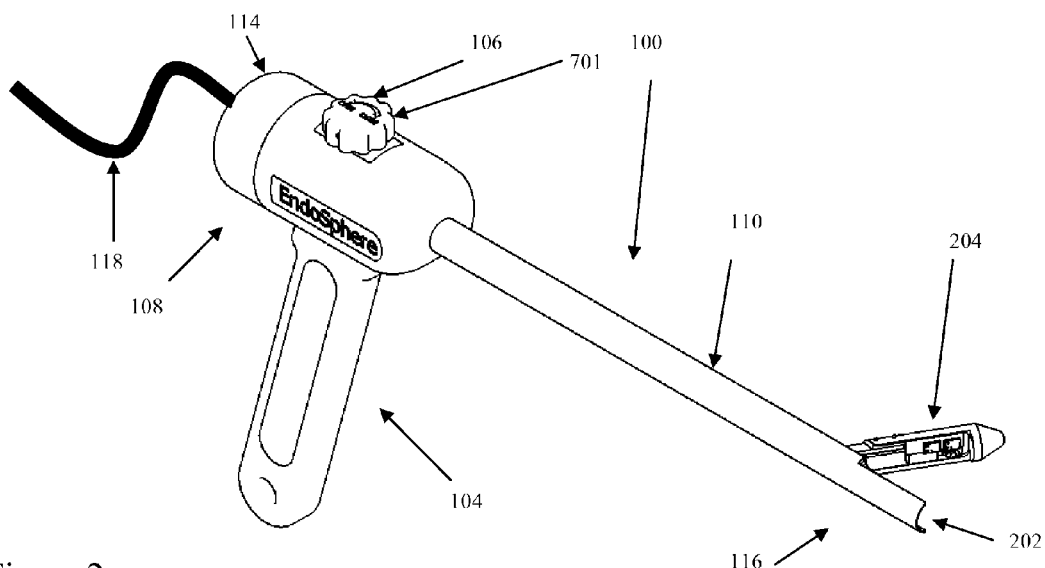
FIG. 2 depicts a schematic perspective view of the cannula assembly of FIG. 1 in one of its open positions.

FIGS. 1 and 2 depict schematic perspective views of an embodiment of the cannula assembly 100 in closed and open positions, respectively. In one embodiment, the cannula assembly 100 includes a tubular element 110 forming a lumen 202. A proximal end 114 of the tubular element 110 can be adapted for manipulation by the surgeon or clinician, and a distal end 116 can be adapted for insertion into a body cavity. A housing 108 with a handle 104 can be attached near or at the proximal end 114 for manipulation by the surgeon or clinician. In alternative embodiments, the tubular element 110 can form a variety of cross-sectional shapes, e.g., generally round or cylindrical, ellipsoidal, triangular, square, rectangular, and D-shaped (in which one side is flat).

All or parts of the distal end of the cannula assembly 100 are capable of being positioned into a closed position 102 for insertion and extraction either directly into the body cavity or through another insufflating cannula. When closed, the distal end assembly forms a pointed tip, such as a trocar capable of puncturing the patient's skin. In another embodiment, the lumen 202 of the tubular element 110 is can be fitted with a retractable and/or removable trocar, such as that depicted in FIGS. 9A-9C and described further hereinbelow. In one embodiment, the trocar is made of solid, non-transparent material; whereas, in another embodiment all or parts of the trocar are made of optically transparent or optically transmissive material.

Figure 3:
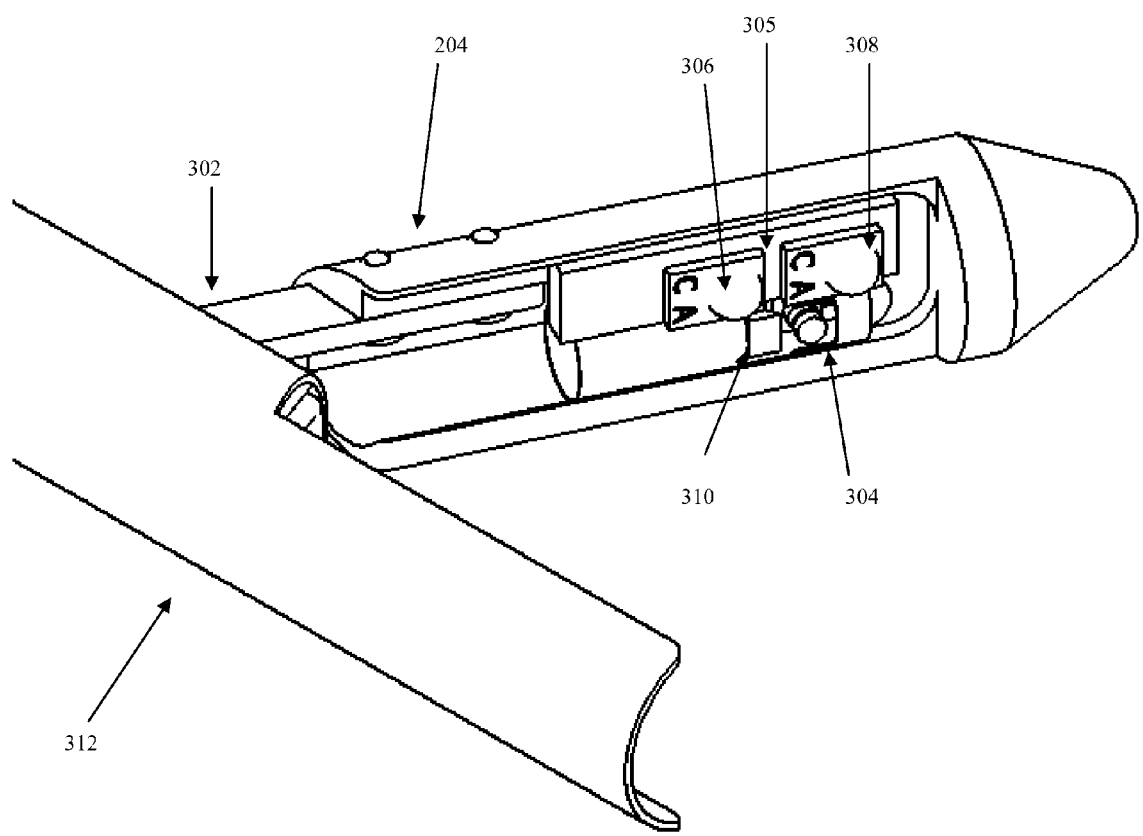
FIG. 3 depicts a close-up schematic perspective view of a tip section of the cannula assembly of FIG. 2.

One or more portions of the distal end 116 of the tubular element 110 may be designed to open once inserted into the body cavity. In one embodiment, as depicted in FIG. 3, at least one deployable portion 204 of the tubular element 110 has an adjustable angle of deployment based on the operation of the opening adjustment means 106, i.e., an actuation mechanism. For example, the adjustment means 106 can move the deployable portion 204 between a closed position and an open position. Alternatively, the adjustment means 106 can incrementally move the deployable portion 204 between a closed position and any number of open positions. In additional or alternative embodiments, the deployable portion 204 houses an electronic component, which is at least partially disposed in the lumen when in the closed position. In an alternative embodiment, all electronic components are housed within the walls of the tubular element. When the deployable portion 204 is moved to at least one open position, the lumen 202 is substantially free from obstruction due to the electronic components being moved out of the lumen, such that various instruments, e.g., surgical tools or other electronic components, can be passed through the lumen and used during the operation or surgical procedure.

The electronics components include one or more image transmission components 304, in combination with one or more illumination components 305. In one embodiment, the image transmission component 304 may be a charge-coupled device (CCD) camera, a complementary metal oxide semiconductor (CMOS) imaging device, and/or an imaging fiber optic cable, and their ancillary optics and electronic drivers for power, communication and other functions.

Optically, one or more of the image transmission components 304 may also image across the spectrum, including those portions invisible to the human eye, such as infrared and ultra-violet. In one embodiment, two image transmission components may be configured to capture stereoscopic images (in still and/or in motion). In one embodiment, one or more of the image transmission components 304 may be configured with any of a combination of fixed optics, adaptive optics, and/or active optics. Adaptive and active optics can be capable of focusing and/or zooming onto the image or target area.

In one embodiment, the one or more image transmission components 304 are capable of capturing both motion and still images, and transmitting them to the surgeon or operator through wired or wireless communication means 118 housed within or connected to the housing 108, handle 104, lumen 202 and/or the tubular element 110 wall. Such communications means 118 may include electrical signals, such as analog and/or digital, or a fiber optic communication system.

The illumination component 305 may be one or more light or illumination sources 306, 308, and their ancillary electronic drivers 310. In one embodiment, the illumination sources 306, 308 are Light Emitting Diodes (LED), organic LED (OLED), illumination fiber optic, filament lamps, electroluminescent and/or laser sources. In one embodiment, the illumination component 305 is tailored to work closely in both optical and spectrum characteristics with the image transmission component 304, with the illumination area, level, and homogeneity being optimized. In one example, this may mean the illumination level is controlled by the surgeon or clinician; whereas, in another the image transmission component Automated Gain Control (AGC) is correlated with the illumination level of the illumination component 305.

Figure 7A:
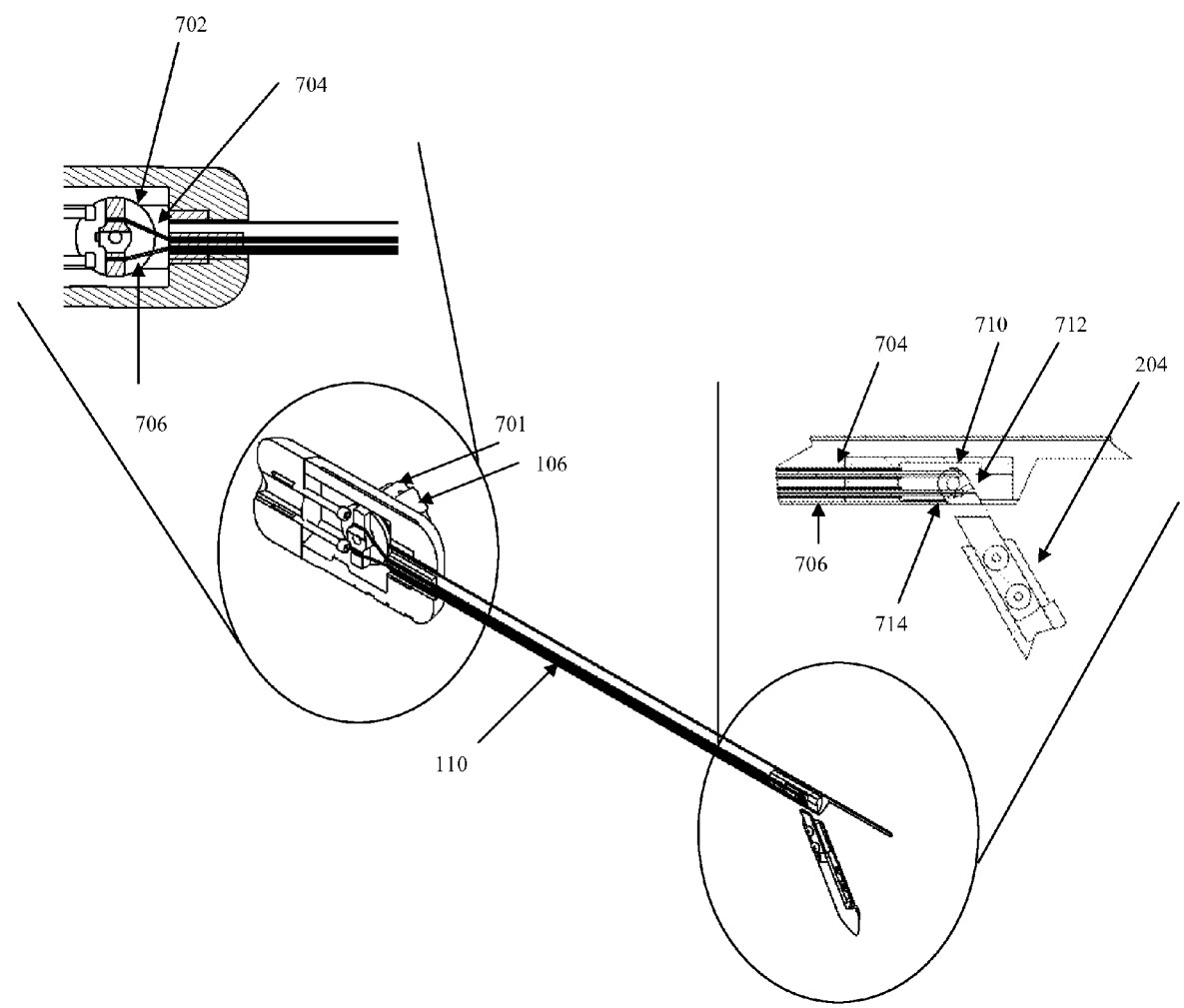
FIGS. 7A and 7B depict schematic cross-sectional close-up and schematic perspective views of an actuating mechanism connected to a deployable portion of a cannula assembly in the open and closed positions, in accordance with an embodiment of the present invention.
Figure 7B:
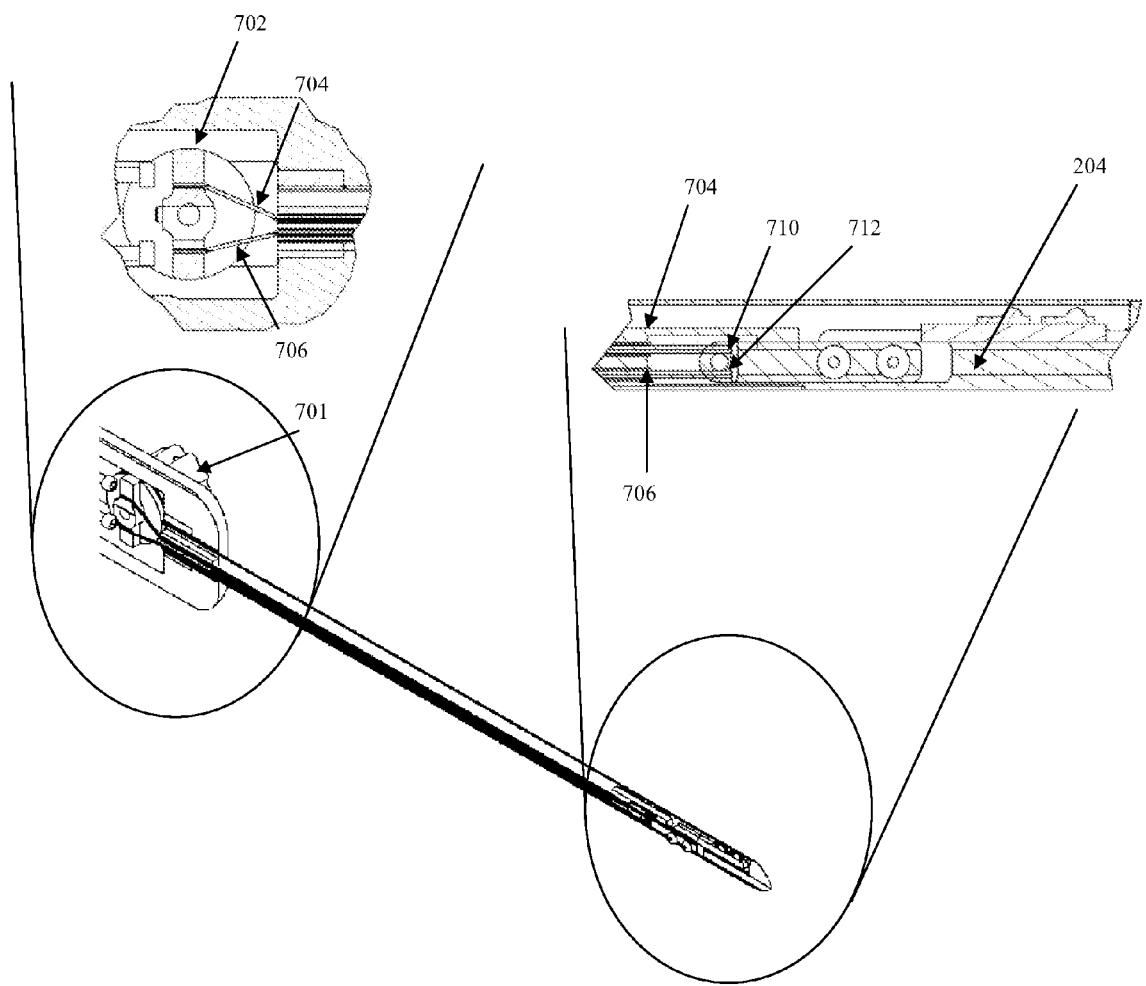

In one embodiment, as depicted in FIGS. 7A and 7B, the adjustment means 106 may include a knob 701, which is connected to a rotational wheel 702, and links 704, 706 traveling through the lumen, along the length of the tubular element 110. In an alternative embodiment, a push rod can be used in lieu of a knob 701. In another alternative embodiment, the links 704, 706 travel through one or more longitudinal apertures formed in the wall of the tubular element 110.

Turning the knob 701 causes rotation of the wheel 702 in one direction, which pulls on one end of the link 706 and transfers force to its other end, which is connected to a downstream portion 712 of a hinge 714, and opens the deployable portion 204. A partial turn of the knob 701 can, for example, move the deployable portion 204 into any intermediate open position. An equivalent, but opposite turn of the knob 701 pulls on link 704, which is connected to an upstream portion 710 of the hinge 714, and closes the deployable portion 204. The links 704 may be stiff or flexible elements, such as bars, rods, cables, wires, etc. Alternatively, a nut and lead screw combination may be used. Instead of the knob 701, a lever can be used. Similarly, instead of the knob 701, a spring-loaded release mechanism can actuate the deployable portion 204. In an alternative embodiment, the deployable portion 204 can be actuated with a magnetic system. In this configuration, the deployable portion 204 is fitted with a magnet (e.g., a permanent magnet or a ferromagnetic target). A complementary magnet (e.g., a permanent magnet or a electromagnet target) external to the body or patient is used to interact with the magnet on the deployable portion 204, such that an operator can open and close the deployable portion 204 by moving the external magnet about and in relation to the deployable portion 204.

The hinge arrangements for the opening/closing of the deployable portions 204 may be accomplished in a number of ways. In one embodiment, one or more of the deployable portions 204 transition between a closed and a number of open positions via a hinge arrangement. The hinge arrangement may include a hinge disposed within a wall of the tubular element 110, e.g., all or partially within the lumen 202, around a pivot point, on a circumference of the tubular element 110, e.g., a circumferential hinge, and/or on an exterior of the tubular element 110. Alternatively, the hinge arrangement may include at least one four-bar linkage.

In an alternative embodiment, the lumen 202 is kept clear by passing the links 704, 706 through a recess along or an aperture formed inside the tubular element 110 wall. In an alternative embodiment, the adjustment means 106 include electro-mechanical actuation of switches, operated by the surgeon or clinician, that drive one or more motors. The motors or actuators may be located either within the proximal end 114 (e.g., non-deployable portions) of the tubular element 110, or within the deployable portion 204. Alternatively, the deployable portion 204 can be moved via a pneumatic or fluidic actuator.

In an alternative embodiment, the hinge connecting the deployable portion 204 to the distal end 116 can include Shape Memory Alloy (SMA) materials with or without an assisted heating element. In one embodiment, using a material such as Nitinol (located within the lumen 202, tubular element 110 and/or the deployable portion 204), any deployable portion 204 can be closed at room temperature (e.g., 25° C.), and deploy at the temperature less than that expected within the body cavity (e.g., less than 37° C.). In an alternative embodiment, the assisted heating element can be controlled by the surgeon or clinician. The voltage for the assisted heating element can be transmitted along the tubular element 110 walls. The assisted heating element is used to place the SMA material into the deployable temperature range once within the body cavity; for example, increasing the voltage will increase the temperature of the SMA material, which transitions the deployable portion 204 to one or more of its open positions. Removing or decreasing the voltage (and hence the heat), makes the deployable portion 204 transition to its closed position.

Figure 6:
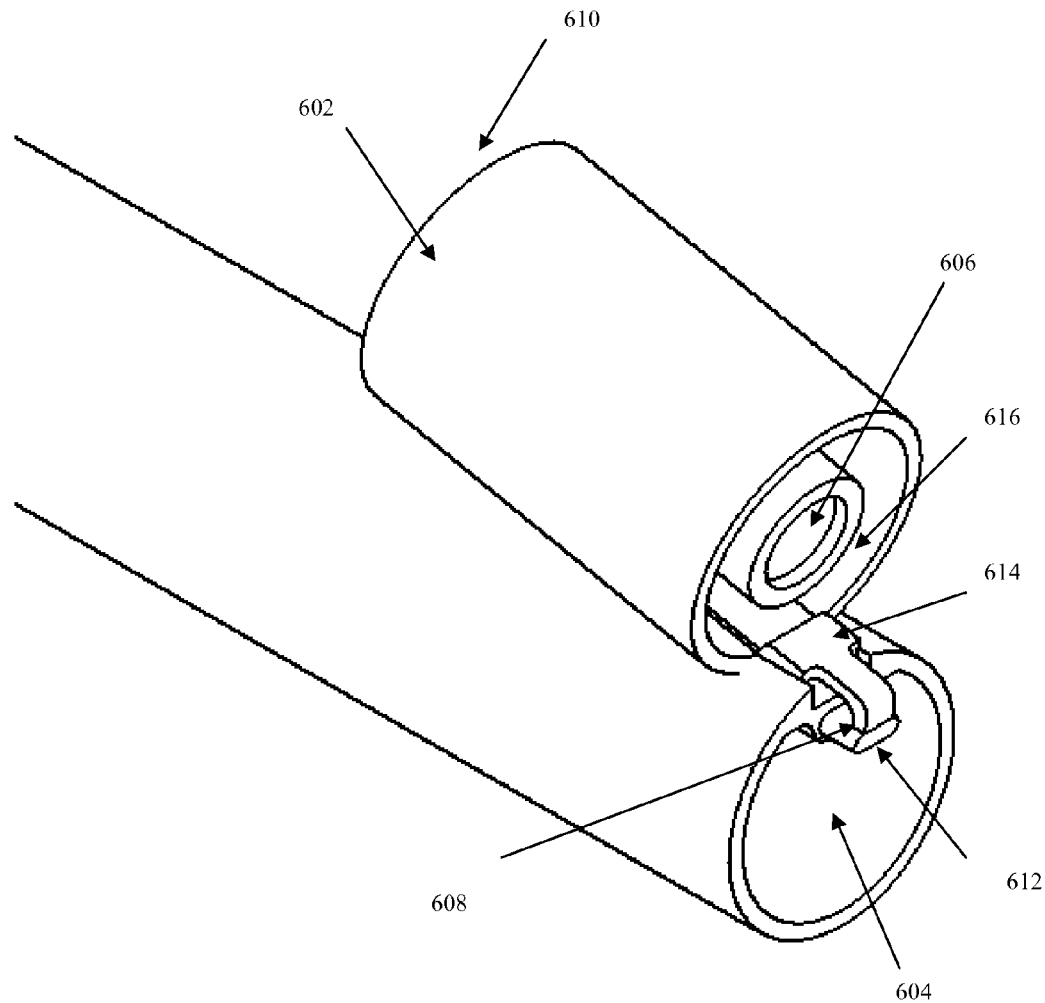
FIG. 6 depicts a schematic perspective close-up view of another embodiment of a tip section of a cannula assembly in one of its open positions, according to an embodiment of the present invention.

In one embodiment, as depicted in FIG. 6, the link 612 is a single element, e.g., a tape or rod, made of metal or other non-buckling configuration, which when pushed towards the distal end by the surgeon via operation of the knob 701, causes it to extend towards the distal end of the lumen 604. The extending pressure forces the hinge arrangement 608, 614 on the deployable portion 602 to flip and to rotate into one or more open positions, causing the formerly distal facing portion 610 to now face towards the proximal end. In this configuration, the imaging component 606 and illumination component 616 face the area of interest. The angle of opening of the deployable portion 602 may be adjusted by the amount of link 612 fed into the tubular element 110 through the rotation of the knob 701 or other structural adjustment mechanism. This arrangement allows for the image component 606 and illumination components 616 to occupy almost or all of the lumen 604 when closed, and to leave the lumen 604 substantially open and available for instrument insertion/operation and/or removal of both instruments and body samples when open. In addition, this arrangement protects any image or illumination components when closed, while allowing the same degree of triangulation by adjustment of either the opening angle for the deployable portion 602 and/or the image component 606 and illumination component 616. Similar hinge arrangements and adjustment means to those described herein may also be used.

Figure 8:
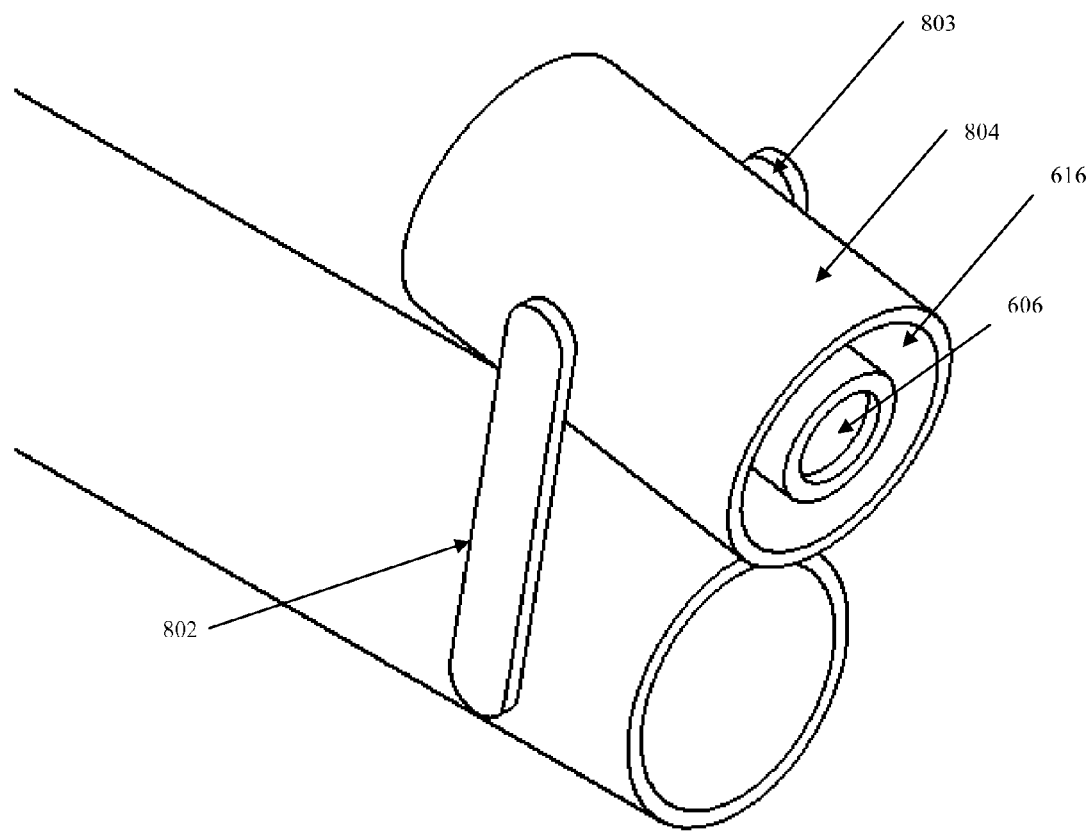
FIG. 8 depicts a schematic perspective close-up view of a tip section of a cannula assembly in one of its open positions, according to another embodiment of the present invention.

In an alternative embodiment, as depicted in FIG. 8, the hinge arrangement is a four-bar linkage with arms 802, 803 that are attached to a deployable portion 804. In this arrangement, the deployable portion 804 can be similarly actuated as described above. For example, one or more links passing internally through the wall of the tubular element 110 connect to the arms 802, 803. Rotation of the knob or a push of a push rod raises the deployable portion 804 above the tubular element 110. Imaging component 606 and illumination component 616 are housed in the deployable portion 804.

Figure 4:
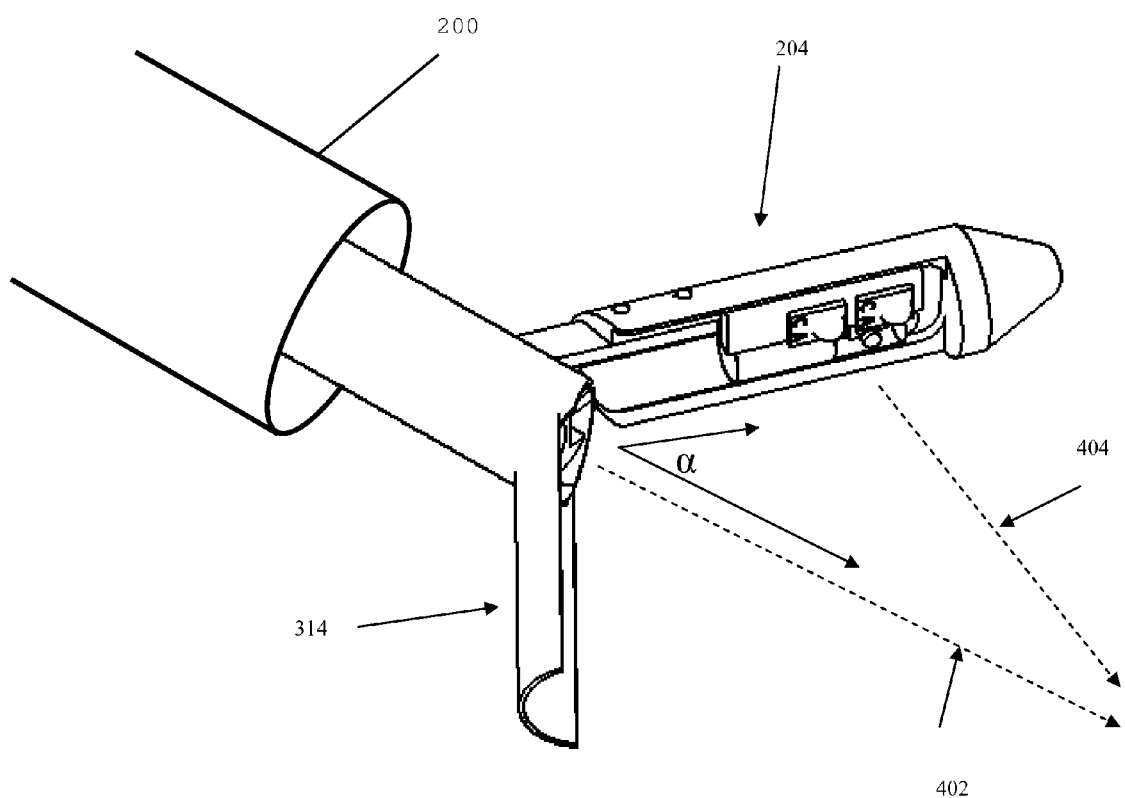
FIG. 4 depicts a close-up schematic perspective view of another embodiment of the tip section of a cannula assembly in one of its open positions, in accordance with an embodiment of the present invention.

In an alternative embodiment, as depicted in FIG. 4, the tubular element 110 can include a plurality of deployable portions, e.g., two or three deployable portions. For example, as shown in FIG. 4, one embodiment includes two deployable portions, one deployable portion 205 with electronic components (e.g., one or more image transmission components and/or one or more illumination components), the other deployable portion 314 without electronic components. Alternatively, both deployable portions 205, 314 can include electronic components. One or both of the deployable portions 205, 314 can open in response to user input. The number of deployable portions is only limited by the ability to divide the circumference of the tubular element 110, in either homogeneous or dissimilar sized portions. One or more such deployable portions may be formed, using any combination of the adjustment means discussed herein. This gives the surgeon or clinician additional freedom from cannula interference in the area where the surgery or operation is taking place.

In one embodiment, the deployable portion 204 containing electronic component is actuated with mechanical links, while the other deployable portion 314, with no electronic component, uses SMA means for deployment. This would allow the fine pointing/triangulation for the deployable portion 204 with electronic components, and a simpler, less precise adjustment mechanism for the other deployable portion 314. In another embodiment, a complementary set of electronics is housed in each deployable portion 204, 314, providing system redundancy selectable by the surgeon or operator. In another embodiment, the tubular element 110 can include three deployable portions, one containing image transmission components, the other containing illumination components, and the last one having no electronic component. Alternatively, at least one or more of an image transmission component and an illumination component can be disposed on each of the deployable portions.

The deployable portion(s) 204 of the tubular element 110 is configured to move from the closed position aligned with the tubular element 110 (i.e., at zero degrees) into an infinite number of open positions from zero to 180 degrees relative to the centerline axis defined by the tubular element 110. This provides the surgeon or operator with the ability to effectively "triangulate" one or more of the field of views of the image transmission component and the illumination component. As may be seen in FIG. 4, adjusting the angle α of the opening of the deployable portion 204 relative to the axis 402 of the tubular element 110, causes the direction of view 404, e.g., of the image transmission component or illumination component, to be adjusted without movement of the cannula. This allows the view to be changed slightly, without reverting to the need to move the cannula. During a procedure, moving the cannula may affect an instrument's position, vis-à-vis the organ or body structure being operated on. In use, the cannula may be rotated so that the image transmission component and the illumination component cover more fields of view. The rotation of the cannula can be tracked to keep the image in one orientation. In various embodiments, an accelerometer, an encoder (e.g., mechanical or optical), or other suitable feedback element disposed in the cannula assembly can communicate with control electronics in the video output of the image transmission component to rotate the image before it is displayed to the operator, in order to maintain the image in the same orientation. The feedback element may have a fixed reference point to indicate a preferred orientation, such as a vertical or up orientation. The fixed reference point of the feedback element corresponds to a particular reference point or orientation of the image transmission component. This may be the same orientation, such as an up orientation. Rotation of the cannula can be accomplished automatically without user-intervention or the rotation can be controlled by the operator. Within the image transmission component, well known and understood imaging features may be implemented, including electro-optic image stabilization and others.

A fail-safe design feature of the cannula assembly results from the hinge arrangement for the deployable portion(s) 204 being located at a point upstream of the distal end 116. The deployable portion 204 can be closed upon extraction of the cannula assembly through the force exerted on it during withdrawal through an external insertion cannula 200. In this configuration, the deployable portion 204 is moved to the closed position without operation of the adjustment means 106.

All or part of the distal end 116 of the tubular element 110 may be formed from an optically transparent material as a trocar, pointed tip, or any suitably shaped frontal form. In combination with a deployable or removable mirror occupying all or part of the interior volume of the lumen 202, the surgeon or operator would be able to see a forward view beyond the cannula assembly when the deployable portion 204 is at or near the closed position. In an alternative embodiment, a prism can be used in lieu of a mirror.

Figure 5A:
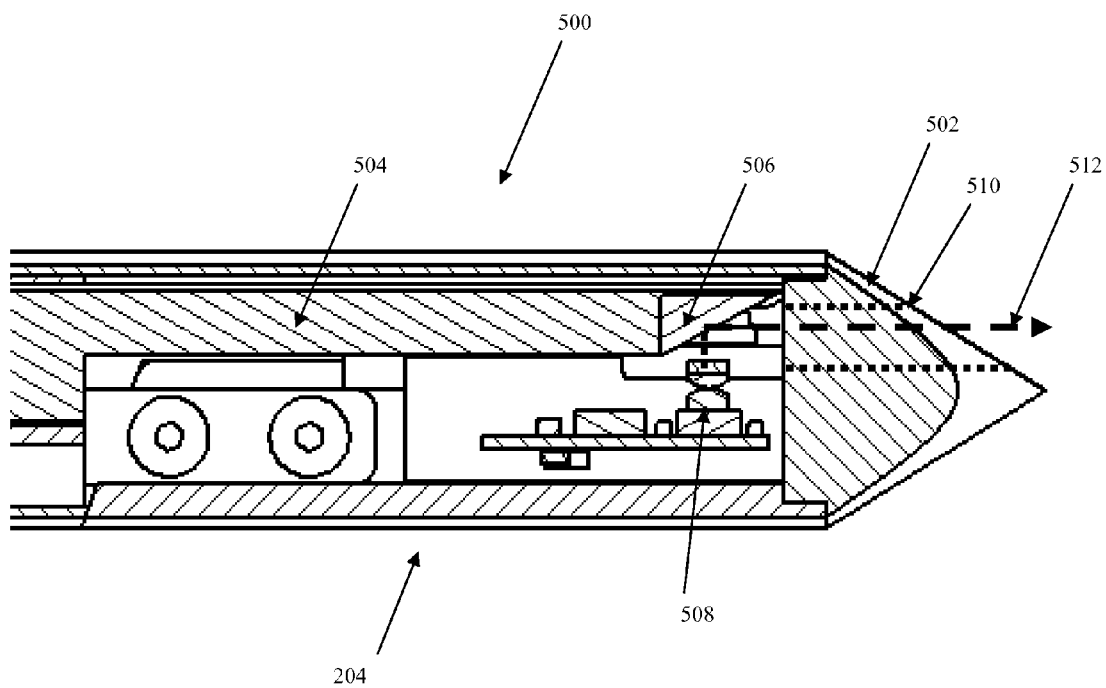
FIGS. 5A and 5B depict schematic cross-sectional and schematic partial sectional perspective views of a tip section of a cannula assembly in which an imaging component is configured for forward viewing while the cannula assembly is in the closed position, in accordance with an embodiment of the present invention.
Figure 5B:
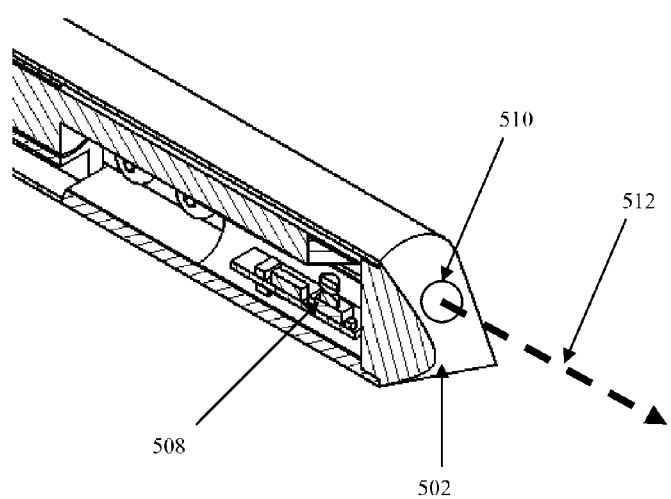

FIGS. 5A and 5B illustrate an embodiment of the cannula assembly 100 in which all or part of the trocar is made of optically transmissive or optically transparent materials. When the deployable portion 204 is in a closed position 500, the image transmission component 508 is capable of imaging through the distal end 502 of the cannula assembly via an optical path 512, which travels through a window 510, light pipe, or similar optically transmissive medium on the distal end 502.

Within the lumen, a mirror assembly, which can be one or more suitably reflective surfaces 506, can be placed at suitable angle(s) to permit the forward view. The reflective surface 506 forms a connection 504 (e.g., a rod) through the lumen 202 of the cannula assembly 100 to the proximal end 114, allowing the mirror assembly to be extracted once the deployable portion 204 is opened, if necessary.

Figure 9A:
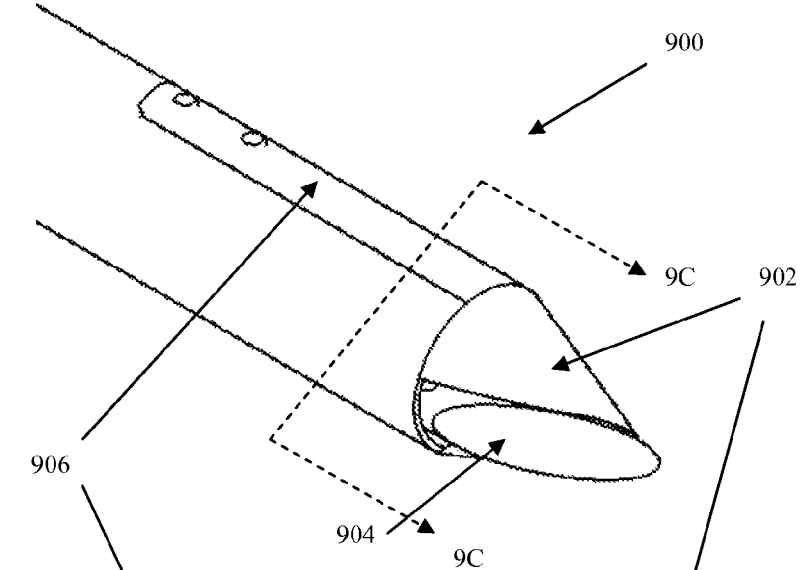
FIGS. 9A, 9B and 9C depict schematic perspective and schematic cross-sectional views of another tip embodiment of the apparatus with the capability of forward viewing while closed and having a removable trocar, according to an embodiment of the present invention.
Figure 9B:
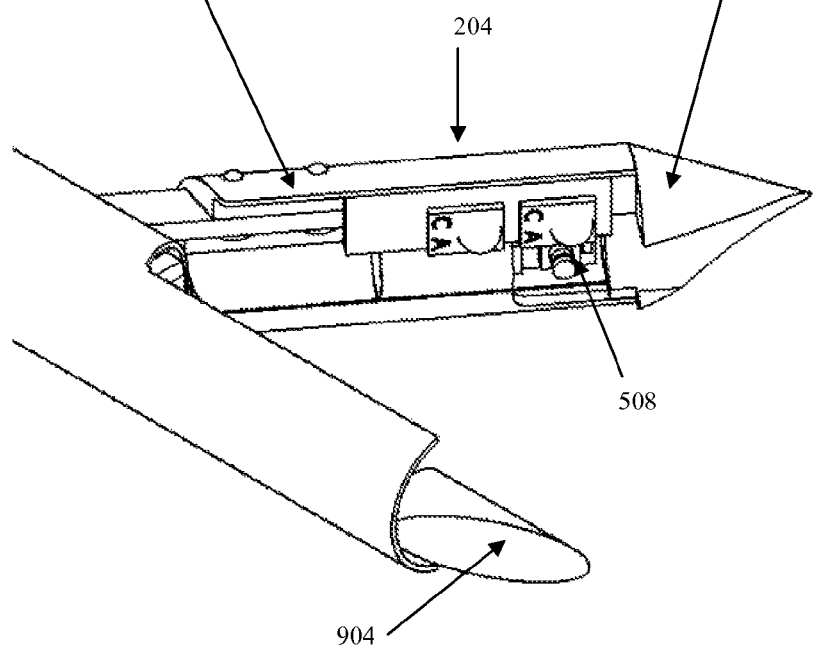
Figure 9C:
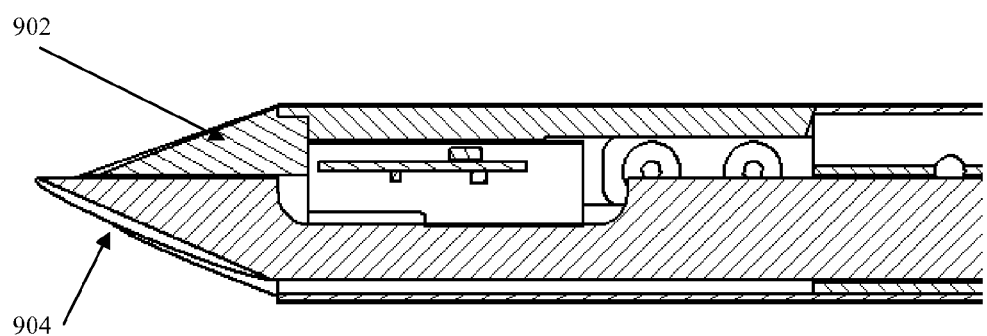

As depicted in FIGS. 9A, 9B and 9C, a cannula assembly 900 has the capability of forward viewing while the deployable portion 204 is in the closed position. In addition, the cannula assembly 900 can include a removable trocar. The distal end forms a combination of two portions. One is a deployable portion 204 (with external surface 902) and the other is a retractable portion 904. The deployable portion 204 may be made from any suitable material, while the retractable portion 904 is preferably made from an optically transmissive or optically transparent material. An optically transmissive or optically transparent material provides a window, that in combination with the mirror assembly inside the lumen (and similar to those described above), allows the imaging transmission component to view forward while the deployable portion 204 is in the closed position. Upon deployment, retractable portion 904 is retracted through the lumen by the surgeon or operator.

In one embodiment, additional illumination sources are placed within indentations in the external surface 904 facing the distal end. Such illumination sources would minimize reflections from the optically transmissive portions of the trocar coming back to the image transmission components. In an alternative embodiment, power for the illumination sources is provided by energy storage components placed within the cannula assembly, e.g., a battery in the handle, minimizing the interfacing to the rest of the cannula assembly. The surgeon can activate the illumination sources at the time of insertion of the cannula assembly. The illumination source may include any of the illumination sources described above. The energy storage component may be batteries or super-capacitors. The energy storage component can be attached to the rod 504 or can be connected to the illumination sources.

Various embodiments and features of the present invention have been described in detail with a certain degree of particularity. The utilities thereof can be appreciated by those skilled in the art. It should be emphasized that the above-described embodiments of the present invention merely describe possible examples of the implementations to set forth a clear understanding of the principles of the invention, and that numerous changes, variations, and modifications can be made to the embodiments described herein without departing from the spirit and scope of principles of the invention. Also, such variations and modifications are intended to be included herein within the scope of the present invention, as set forth in the appended claims. The scope of the present invention is defined by the appended claims, rather than the forgoing description of embodiments. Accordingly, what is desired to be secured by Letters Patent is the invention as defined and differentiated in the following claims, and all equivalents

What is claimed is:

1. A cannula assembly comprising:
   a proximal end and a distal end adapted to be inserted into a body cavity and defining a longitudinal axis;
   a tubular element forming a lumen extending from the proximal end to the distal end;
   a deployable portion of the assembly rotatable about a single axis transverse to the longitudinal axis, wherein the deployable portion is coupled to and movable with respect to the distal end so as to transition between a closed position and an open position; and
   an electronic component comprising an image transmission component mounted to the deployable portion of the assembly, wherein when the deployable portion is in the closed position, the electronic component: (i) at least partially blocks the lumen; (ii) is enclosed in an interior of the assembly so as to be protected from contact at least when the distal end of the assembly is inserted into the body cavity; and (iii) is adapted to provide a forward view;
   wherein the deployable portion comprises a wall portion of the tubular element and forms a pointed tip at the distal end of the tubular element when the deployable portion is in the closed position.

2. The cannula assembly of claim 1, wherein the open position comprises a range of angular positions.

3. The cannula assembly of claim 1, wherein the electronic component is disposed remotely from the lumen when the deployable portion is in the open position.

4. The cannula assembly of claim 1 further comprising a removable trocar adapted to fit into the lumen when the deployable portion is in the closed position.

5. The cannula assembly of claim 1, wherein the pointed tip comprises an optically transparent material, so as to project an image through the pointed tip onto the image transmission component when the deployable portion is in the closed position.

6. The cannula assembly of claim 1, wherein the electronic component further comprises at least one of an illumination component and a feedback element.

7. The cannula assembly of claim 6, wherein the illumination component is selected from the group consisting of a light source and a fiber optic cable.

8. The cannula assembly of claim 7, wherein the light source is selected from the group consisting of a light emitting diode, an organic light emitting diode, a filament lamp, an electroluminescent source, and a laser source.

9. The cannula assembly of claim 1, wherein the image transmission component is selected from the group consisting of a charge-coupled device camera, a complementary metal oxide semiconductor imaging device, and a fiber optic cable.

10. The cannula assembly of claim 1, wherein the deployable portion of the assembly transitions between the open position and the closed position via a hinge arrangement.

11. The cannula assembly of claim 10, wherein the hinge arrangement is disposed in the tubular element.

12. The cannula assembly of claim 11, wherein the hinge arrangement comprises a pivot.

13. The cannula assembly of claim 10, wherein the hinge arrangement is disposed on a circumference of the tubular element.

14. The cannula assembly of claim 13, wherein the hinge arrangement comprises a circumferential hinge.

15. The cannula assembly of claim 10, wherein the hinge arrangement is disposed on an exterior of the tubular element.

16. The cannula assembly of claim 15, wherein the hinge arrangement comprises at least one linkage.

17. The cannula assembly of claim 10, wherein the assembly comprises a fail-safe feature wherein the hinge arrangement is disposed upstream of the distal end which permits removal of the assembly from the body cavity when the deployable portion is in the open position without damage to the assembly.

18. The cannula assembly of claim 1 further comprising an actuation mechanism configured to transition the deployable portion between the closed position and the open position.

19. The cannula assembly of claim 18, wherein the actuation mechanism comprises:
   a knob disposed near the proximal end;
   at least one link coupled to the knob; and
a hinge arrangement coupled to the at least one link and the deployable portion, wherein rotation of the knob moves the deployable portion between the open position and the closed position.

20. The cannula assembly of claim 1, wherein the electronic component is protected in the closed position.

21. The cannula assembly of claim 1, wherein the image transmission component is operable in the closed position.

22. The cannula assembly of claim 1, wherein the image transmission component is operable in the open position.

23. The cannula assembly of claim 1, wherein the electronic component further comprises at least one feedback element to maintain orientation of an image.

* * * * *